United States Patent
Bornzin et al.

(10) Patent No.: US 9,211,406 B2
(45) Date of Patent: Dec. 15, 2015

(54) MRI COMPATIBLE IMPLANTABLE LEAD

(71) Applicant: PACESETTER, INC., Sylmar, CA (US)

(72) Inventors: Gene A. Bornzin, Simi Valley, CA (US); Zoltan Somogyi, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/080,676

(22) Filed: Nov. 14, 2013

(65) Prior Publication Data

US 2014/0277312 A1 Sep. 18, 2014

Related U.S. Application Data

(60) Provisional application No. 61/784,985, filed on Mar. 14, 2013.

(51) Int. Cl.
*A61N 1/00* (2006.01)
*A61N 1/08* (2006.01)
*A61N 1/05* (2006.01)

(52) U.S. Cl.
CPC .. *A61N 1/08* (2013.01); *A61N 1/05* (2013.01); *A61N 1/056* (2013.01); *A61N 1/0573* (2013.01); *A61N 2001/086* (2013.01); *Y10T 29/49174* (2015.01)

(58) Field of Classification Search
USPC .................................. 607/116, 119; 600/372
See application file for complete search history.

(56) References Cited

U.S. PATENT DOCUMENTS

| | | |
|---|---|---|
| 2006/0229693 A1 | 10/2006 | Bauer et al. |
| 2007/0255377 A1 | 11/2007 | Marshall et al. |
| 2009/0270956 A1 | 10/2009 | Vase et al. |
| 2010/0049290 A1 | 2/2010 | Min et al. |
| 2011/0118813 A1 * | 5/2011 | Yang et al. ............... 607/116 |
| 2011/0125240 A1 | 5/2011 | Zhao et al. |

FOREIGN PATENT DOCUMENTS

EP 2446920 A1 5/2012

OTHER PUBLICATIONS

Partial EP Search Report, mailed Aug. 4, 2014—EP App No. 14159562.9.

* cited by examiner

*Primary Examiner* — Nicole F Lavert

(57) ABSTRACT

An implantable lead is provided that comprises a lead body configured to be implanted in a patient, the lead body having a distal end and a proximal end, and a lumen extending between the distal and proximal ends; a connector assembly provided at the proximal end of the lead body, the connector assembly configured to connect to an implantable medical device; an electrode provided along the lead body, the electrode configured to at least one of deliver stimulating pulses and sense electrical activity, the electrode having a length extending between a proximal end and a distal end of the electrode; a conductor cable located within the lead body and extending at least partially along a length of the lead body; and an connection node electrically connecting the cable to the electrode at an intermediate point along the length of the electrode. The connection node is disposed at a position intermediate between the proximal and distal ends of the electrode.

8 Claims, 10 Drawing Sheets

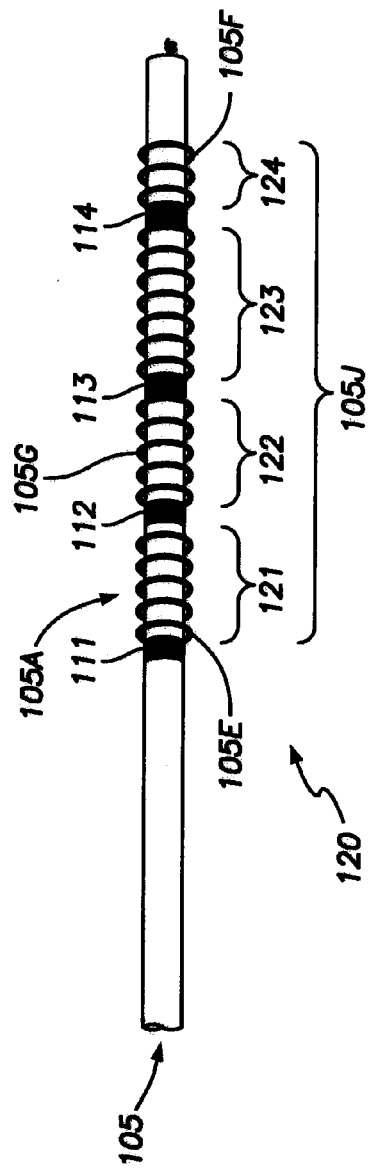
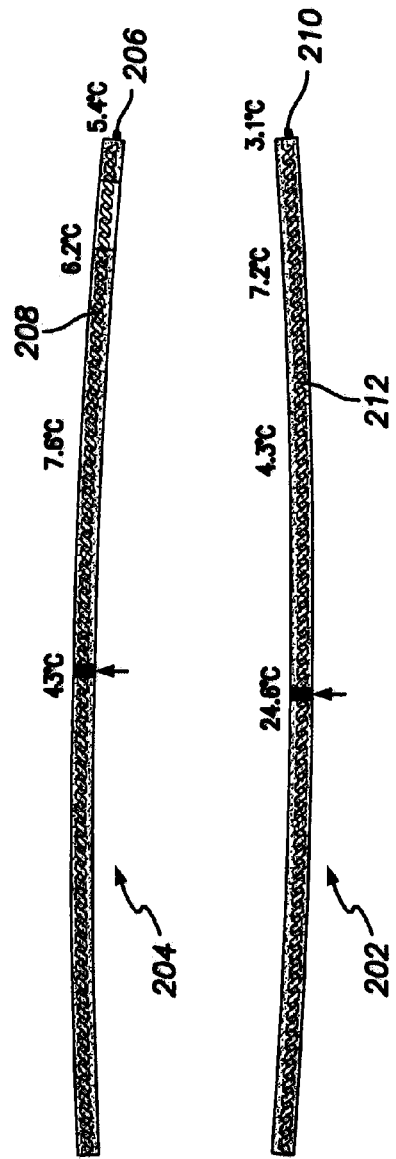
FIG. 1C
FIG. 2

MRI COMPATIBLE IMPLANTABLE LEAD

CROSS-REFERENCE TO RELATED APPLICATION

The present application claims the benefit of U.S. Provisional Application Ser. No. 61/784,985, filed on Mar. 14, 2013, entitled "MRI Compatible Implant Lead". The subject matter of this provisional application is incorporated herein by reference in its entirety.

BACKGROUND OF THE INVENTION

Embodiments of the present invention generally relate to MRI compatible leads and more particularly to leads that exhibit low heating when exposed to MRI fields.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like (hereafter generally "implantable medical devices" or "IMDs". IMDs commonly employ one or more conductive leads that either receive or deliver voltage, current or other electromagnetic pulses from or to an organ or its surrounding tissue for diagnostic or therapeutic purposes. The leads include bare or insulated coiled wire forming one or more tightly wound solenoid-like structures along the shafts. These tightly wound coils facilitate torque transfer, prevent "buckling" and allow the conduction of electrical signals to and from the proximal (system) end to the distal (patient) end of the device. The lead may represent a catheter, an ICD lead, a neurostimulation lead, a pacemaker lead and the like. When exposed to electromagnetic fields, such as for example those present in magnetic resonance imaging ("MRI") systems, these leads may sustain undesired currents and/or voltages that interact with the surrounding blood and tissue, potentially resulting in unwanted tissue heating, nerve stimulation or other negative effects resulting in erroneous diagnosis or therapy delivery.

Existing implantable medical leads for use with implantable pulse generators, such as neurostimulators, pacemakers, defibrillators or implantable cardioverter defibrillators ("ICD"), are prone to heating and induced current when placed in the strong magnetic (static, gradient and RF) fields of a magnetic resonance imaging ("MRI") machine. The heating and induced current are the result of the lead acting like an antenna in the magnetic fields generated during a MRI. Heating and induced current in the lead may result in deterioration of stimulation thresholds or even increase the risk of cardiac tissue damage.

Over fifty percent of patients with an implantable pulse generator and implanted lead require, or can benefit from, an MRI in the diagnosis or treatment of a medical condition. MRI modality allows for flow visualization, characterization of vulnerable plaque, non-invasive angiography, assessment of ischemia and tissue perfusion, and a host of other applications. The diagnosis and treatment options enhanced by MRI are only going to grow over time. For example, MRI has been proposed as a visualization mechanism for lead implantation procedures.

A need remains for an improved MRI compatible lead that addresses the above problems and other issues that will be apparent from the following discussion and figures.

SUMMARY

In accordance with an embodiment, an implantable lead is provided. The implantable lead comprises a lead body configured to be implanted in a patient, the lead body having a distal end and a proximal end, and a lumen extending between the distal and proximal ends; a connector assembly provided at the proximal end of the lead body, the connector assembly configured to connect to an implantable medical device; an electrode provided along the lead body, the electrode configured to at least one of deliver stimulating pulses and sense electrical activity, the electrode having a length extending between a proximal end and a distal end of the electrode; a conductor cable located within the lead body and extending at least partially along a length of the lead body; and an connection node electrically connecting the cable to the electrode at an intermediate point along the length of the electrode, the connection node disposed at a position intermediate between the proximal and distal ends of the electrode.

Optionally, the cable may include a distal end that is joined at the connection node to the intermediate point along the electrode. The electrode may include turns that extend about the lead body, the connection node electrically coupled to an intermediate turn within the electrode. The electrode may include turns that extend about the lead body, the cable being electrically connected at first and second connection nodes to first and second intermediate turns spaced apart from one another and apart from the distal and proximal ends of the electrode.

Alternatively, the electrode may include turns and the connection node may include a conductive ring provided about the lead body, where the connection node is positioned between adjacent intermediate turns of the electrode, and the ring is electrically connected to the cable and electrically connected to at least one turn of the electrode. Optionally, the cable may include at least first and second filers, the first and second filers including distal ends connected at the connection node to the electrode. Optionally, the first and second filers may include distal ends connected at first and second separate connection nodes to the electrode, respectively. The lead includes a connector at proximal end. The connector is configured to be connected to at least one of an implantable or external medical device, the lead representing at least one of a catheter, an ICD lead, a neurostimulation lead, a pacemaker lead and a defibrillator lead.

In accordance with an embodiment, a method is provided which provides an implantable lead, the lead having a lead body to be implanted in a patient, the lead body having a distal and a proximal end, the lead body having a connector assembly at the proximal end of the lead body to connect to an implantable medical device, the lead body having a conductor cable within the lead body and extending at least partially along a length of the lead body. The method comprises: locating an electrode along the lead body, where the electrode is configured to at least one of deliver stimulating pulses and sense electrical activity. The electrode has a length extending between a proximal end and a distal end of the electrode. The method positions a connection node within an intermediate segment along the length of the electrode, connects the cable electrically to the connection node, and connects the connection node electrically to the electrode within an intermediate segment along the length of the electrode to form heat dissipating segments within the electrode. The head dissipating segments dissipate heat that is generated within the lead when the lead is exposed to an MRI field.

Optionally, the method may comprise joining at least a distal end of the cable to the connection node. The electrode may include turns that extend about the lead body, the connection node electrically coupled to an intermediate turn within the electrode. Optionally, the connecting operation includes electrically connecting the cable to first and second connection nodes, and electrically connecting the first and second connection nodes to first and second intermediate turns of the electrode. The first and second intermediate turns are spaced apart from one another and apart from distal and proximal ends of the electrode.

The method may comprise forming the connection node from a conductive ring provided about the lead body, positioning the connection node between adjacent intermediate turns of the electrode, and electrically connecting the cable and the intermediate turns of the electrode to the conductive ring. Alternatively, the cable may include at least first and second filers, the method including connecting the first and second filers to first and second connection nodes and first and second turns of the electrode, respectively. Optionally, the method may include connecting the first and second filers to a common connection node and a common turn of the electrode.

In accordance with an embodiment, an implantable lead is provided that comprises a lead body configured to be implanted in a patient, the lead body having a distal end and a proximal end, and a lumen extending between the distal and proximal ends; a connector assembly provided at the proximal end of the lead body, the connector assembly configured to connect to an implantable medical device; a cable within the lead body extending between the connector assembly and the distal end; a tip electrode provided at a distal end of the lead body, the electrode configured to at least one of deliver stimulating pulses and sense electrical activity, the electrode having a helix body configured to securely engage tissue; an obturator slibably received in the helix body of the tip electrode, the obturator having an arm configured to move between extended and retracted positions relative to the helix body of the electrode; and an inductor element located proximate the distal end of the lead and connected to be electrically common with the tip electrode, the inductor element including a biocompatible bobbin and a wire wound about a barrel of the biocompatible bobbin to form a coil, the wire connected to the tip electrode and the cable, the bobbin having a passage there through, the passage configured to receive a stylet utilized to move the obturator to the extending position.

BRIEF DESCRIPTION OF THE DRAWINGS

FIG. 1C illustrates a distal portion of a lead formed in accordance with an embodiment herein.

FIG. 2 illustrates conductive cable configurations for leads utilized in accordance with alternatively embodiments wherein the cable configurations have different numbers of filers.

DETAILED DESCRIPTION

Embodiments described herein concern a lead with multiple separate elements that provides MRI compatibility. The separate elements operate in combination to create a lead for an IMD that exhibits very low heating when exposed to MRI fields induced by MRI systems, such as 3T MRI systems, 1.5 T MRI systems and the like.

Figure 1A:
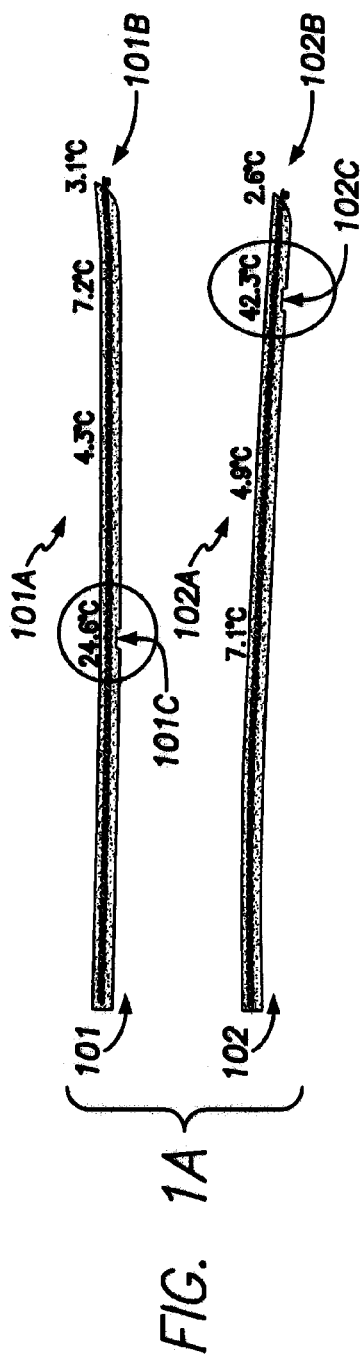
FIG. 1A illustrates distal portions of conventional leads.
Figure 1B:
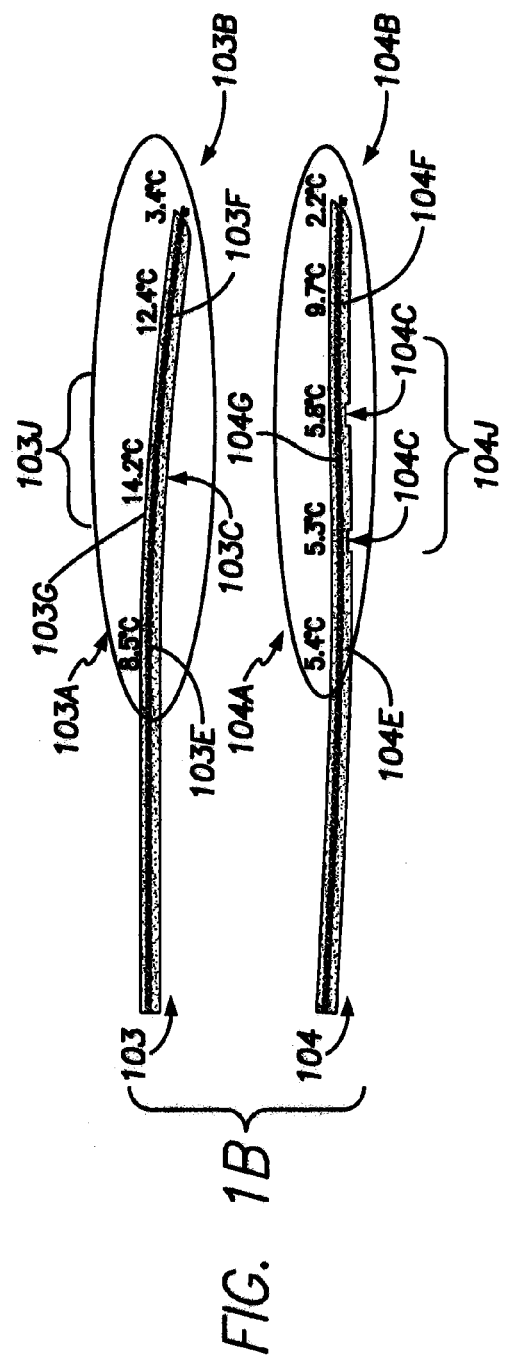
FIG. 1B illustrates distal portions of leads formed in accordance with embodiments herein.

FIG. 1A illustrate distal portions of conventional leads 101 and 102. FIG. 1B illustrate distal portions of leads 103 and 104 formed in accordance with embodiments herein. The leads 101-104 include a coil electrode 101A-104A and tip electrodes 101B-104B. The coil electrode 101A-104A and tip electrodes 101B-104B are joined to corresponding conductive cables that extend along interior lumen within the body of the leads 101-104. In the examples of FIGS. 1A and 1B, the coil electrodes 101A-104A represent shocking coil type electrodes that are configured to deliver therapy at energy levels greater than the energy levels normally associated with pacing pulses.

The leads 101-104 each includes multiple conductive cables extending between the proximal and distal ends. The cables may be multifiler coiled cables that are connected to independent corresponding electrodes that are utilized for sensing and/or delivery of therapy. As one example, the coiled cable may be connected to a shocking coil that is configured to deliver a shocking stimulus having a medium to high energy. Sub-sets of the conductive cables are maintained electrically separate from one another and electrically couple corresponding ones of the coil and tip electrodes 101A-104A and 101B-104B to IMDs that are joined to the proximal ends of the associated leads 101-104.

The leads 101 and 102 of FIG. 1A utilize conventional cable-to-electrode connection configurations between the conductive cable and the coil electrodes 101A and 102A. The lead 101 connects the conductive cable to the proximal end of the coil electrode 101A (at the connection node 101C), while lead 102 connects the conductive cable to the distal end of the coil electrode 102A (at the connection node 102C).

The leads 103 and 104 of FIG. 1B utilize cable-to-electrode connection configurations between the conductive cable and the coil electrodes 103A and 104A in accordance with embodiments described herein. The lead 103 connects the conductive cable at an intermediate node that is located within an intermediate segment 103J along the length of the coil electrode 103A (at the connection node 103C), while lead 104 connects the conductive cable at a pair of intermediate nodes that are located with an intermediate segment 104J along the length of the coil electrode 104A (at the connection nodes 104C).

The shocking coil electrodes 103A, 104A may include an electrode body 103G, 104G that is shaped in a spiral pattern with a predetermined pitch and diameter. The electrode body 103G, 104G includes distal and proximal ends 103E, 104E and 103F, 104F located at opposite ends thereof. The electrode winding includes an intermediate or mid-section generally denoted by segments 103J, 104J. An end of the internal cable is joined at the connection node 103C, 104C to intermediate or mid-section(s) of the electrode body 103J, 104J. The connection node 103C is generally located proximate to a center of the electrode 103A (e.g., RV shocking coil) as one example. The connection nodes 104C are generally located a third of the length from each end of the electrode 104A as another example. By connecting the cable to the center, or at one or more mid-section connection points within segments 103J, 104J, of the electrodes 103A, 104A, embodiments described herein substantially limit heating of the electrodes 103A, 104A, during MRI scanning. The connection node 103C electrically (and thermally) couples the cable to an intermediate turn within the electrode (e.g., a turn spaced evenly between proximal and distal ends of the electrode). The connection nodes 104C electrically (and thermally) connect the cable to first and second intermediate turns spaced apart from one another and apart from the distal and proximal ends of the electrode 104A.

While the foregoing embodiment describes the use of a multifiler coiled cable, alternatively a single filer coiled cable may be utilized.

The tip electrodes 101B-104B represent distal fixation screws. The fixation screw (tip electrode) 101B-104B is joined to a coiled conductor cable that extends from the proximal end of the lead. The fixation screws 101B-104B are joined serially to a corresponding inductor element and the conductor cable (not shown in FIGS. 1A and 1B). The inductor element is located proximate to the distal end of the lead and proximate to the fixation screws 101B-104B. The inductor element is configured with electrical properties that prevent the fixation screw 101B-104B from undergoing significant MRI heating.

The electrode may be configured to deliver high energy shocks. The electrode may be formed in various manners and have various shapes. In general, the electrodes are elongated and tubular in shape. The electrodes may have a continuous body or have a body with spaces or gaps therein to form a desired shape that is flexible but still electrically contiguous or common. For example, the electrode may be formed as a winding that is wound in a spiral manner. Optionally, the electrode may be formed from a solid tubular body structure that is laser cut, stamped and formed, or otherwise modified to remove portions of the tubular body. Optionally, the electrode may be formed from a metal ribbon and the like. The electrode may be formed in other manners provided that the resulting electrode has a framework that resists inward radial compression, may be flexible transverse to the longitudinal axis, is electrically contiguous or common along the length and exhibits desired thermal transfer properties.

Optionally, more than two connection nodes may join the cable and electrode. For example, the connection nodes may be spaced evenly (or unevenly) to separate the electrode into four quadrants. Optionally, connection nodes may be provided at one or both ends of the electrode, as well as at one or more intermediate points along the electrode, to facilitate distribution of MRI induced energy or power.

FIG. 1C illustrates an electrode/cable segment 120 of a lead 105. An electrode 105A has a body 105G with distal and proximal ends 105E, 105F and an intermediate segment 105J. The electrode 105A is joined to the cable at the proximal end 105E, and at three points within the intermediate segment 105J as shown at connection nodes 111-114. The connection nodes 111-114 electrically (and in part thermally) couple the cable to corresponding intermediate turns within the electrode 120 spaced apart from one another and apart from the distal and proximal ends of the electrode 120. The electrode body 105G is apportioned into heat dissipation segments (HDS) 121-124. The HDS 121-124 provide select amounts of thermal absorption or dissipation capacity. Each HDS 121-124 dissipates a portion of the total MRI induced energy at or near the nodes 111-114. For example, HDS 122 and 123 dissipate energy from node 113. The HDS 123 and 124 dissipate energy from node 114, while HDS 121 dissipates energy from node 111. The nodes 111-114 may be evenly or unevenly distributed across the electrode body 105G. The length of each HDS 121-124 may vary, based in part on an expected amount of energy or heat that will be generated at an associated connection node(s). For example, less heating may be expected proximate one node (e.g., 114) relative to heating experienced proximate to another node (e.g., 113).

In accordance with embodiments herein, one or more nodes 111-114 are provided to spread the MRI field induced energy across the electrode 105. The MRI field induced energy is generated by an MRI field while the lead 105 is exposed to the MRI field. The MRI field may introduce a generally set amount of energy or power (e.g., 8-10 Watts), based on the MRI field and lead characteristics, into the electrode/cable segment 120. The nodes 111-114 and HDS 121-124 divide the energy or power based on the number, size and spacing of the nodes and segments. For example, when 2 nodes are used, the energy/power is divided somewhat evenly between the nodes (e.g., 5 Watts is dissipated at each node). Alternatively, when 3 or 4 nodes are used, if the total power is 10 Watts, then each node generally dissipates 3 ⅓ Watts (when 3 nodes are present), or 2 ¼ Watts (when 4 nodes are present). As more nodes 111-114 are added, to an extent, the total power/energy introduced into any single HDS 121-124 is reduced. For example, when 10 Watts total are introduced by the MRI field, HDS 121-124 each receives less energy or power as compared to a configuration in which two HDS are provided (e.g., when a single node is provided in the intermediate segment of the electrode).\

The energy/power introduced into the electrode manifests as current that flows from the electrode into the blood and tissue surrounding the electrode. An amount of current that flows from the electrode is not uniformly distributed over an entire length and surface area of the electrode. Instead, an amount of current flow per unit (or local) area is greater in areas immediately adjacent to the connection nodes (e.g., nodes 111-114), as compared to an amount of current flow per unit (or local) area in areas spaced apart from the connection nodes. The amount of current flow per unit area is also referred to as unit area current.

As current flows from one or multiple local area of the electrode into the blood or tissue, the current flows from a low resistance medium (the electrode) to a relatively higher resistance medium (blood or tissue). As the current flows in to the higher resistance medium (blood or tissue), heating occurs within the blood or tissue and at the local surface of the electrode. An amount of heating is a function, in part, of the local current. Unit areas with relatively higher local current will experience more heating as compared to an amount of heat experienced at blood and tissue unit areas along the electrode that carry lower local current.

Returning to the example embodiments, as a set amount of power is divided between more connection nodes, less current is conveyed from any single connection node (or associated portion of the electrode) to the blood or tissue. Consequently, less heating is experienced at any single connection node (or associated portion of the electrode).

The blood surrounding the electrode transfers or dissipates the heat or thermal energy from the points within the HDS 121-124 of the electrode proximate to the connection nodes 111-114. As a maximum temperature (or energy) experienced by a single HDS 121-124 is lowered, the blood is able to more effectively dissipate the energy/heat. For example, when one connection node is used to form a pair of HDS, the surrounding blood pool at the local areas will provide a certain level of thermal energy transfer from the pair of HDS, whereas when 2 or 3 connection nodes are used to partition the electrode into 4 or 5 HDS, the surrounding blood pool at the local areas may provide a greater (or more efficient) level of thermal energy transfer.

The shocking coil electrode configurations of FIGS. 1A and 1B were tested for heating as follows. In this test, the tip electrodes were not connected to an inductive element as described below in connection with FIG. 2. The leads were placed in a circular phantom in a MRI "birdcage". The leads were "scanned" for six minutes in a 150V/m, 62.5 MHz electric field. The leads were connected to an ICD while the lead was placed at the perimeter of a circular phantom. The "scans" were repeated at several positions as the lead was progressively wrapped around an ICD. The temperature rise illustrated in FIGS. 1A and 1B represents the maximum temperature rise that was recorded, relative to room temperature, when the lead and ICD were exposed to the most power from the electric field. FIGS. 1A and 1B illustrate an amount of local temperature rise ($\Delta T$) experiences by each lead in the corresponding regions of the lead. The temperature measurements in FIGS. 1A and 1B represent examples of temperature differentials relative to a reference temperature, such as room temperature. For example, in FIG. 1A, the temperature 24.6° C. represents a "delta T", temperature differential greater than room temperature.

The lead 101 included two inner conductors connected at 101C to the proximal end of the shocking coil 101A. When placed in a 1.5 T 150 V/m, 62.5 MHz MRI simulator in a phantom for 6 minutes, the lead 101 experienced a maximum temperature rise of 24.6° C. (relative to room temperature) near the circled region (where the inner conductors are connected to the proximal portion of the shocking coil). The lead experienced temperature rises of 4.3° C., 7.2° C. and 3.1° C. at other locations along the lead 101.

The lead 102 included two inner conductors connected at 102C to the distal end of the shocking coil. Lead 102 demonstrates a temperature rise ($\Delta T$) at the distal connection of 42.3° C. (in the circled area). The lead 102 experienced temperature rises of 7.2° C., 4.9° C. and 2.6° C., relative to room temperature, at other locations along the lead 102.

The lead 103 included two inner conductors connected at 103C to the center portion of the shocking coil. The lead 103 demonstrates a 14.2° C. degree temperature rise when being scanned at 150 V/cm. The lead 103 experienced temperature rises of 8.5° C., 12.4° C. and 3.4° C., relative to room temperature, at other locations along the lead 103.

Finally, the lead 104 included two inner conductors that were connected at two points 104C to the central portion of the shocking coil. The lead 104 exhibits a very minimal temperature rise of 9.7° C., relative to room temperature. One of the inner filers servicing one of the connections, another inner filer services the second connection. The lead 104 experienced temperature rises of 5.4° C., 5.3° C., 5.8° C., and 2.2° C. at other locations along the lead 104. These results show that multiple connections in the center of the ICD coil dissipated power over a larger surface area. Inside the heart, flowing blood provides a means of removing heat from the surface of the shocking coil by convection, so the coil would remain relatively cool in the body and undergo about ⅓ or less the temperature rise achieved in the stagnant gel. Modeling predicts about a 3° C. rise, a temperature increase that would do no harm.

FIG. 2 illustrates conductive cable configurations for leads 202 and 204 utilized in accordance with alternatively embodiments wherein the cable configurations have different numbers of filers. The leads 202 and 204 have co-radial coil DFT cables. The lead 202 includes four filers, while the lead 204 includes 2 filers. The leads 202 and 204 have identical pitch, namely 16 turns per inch for each filer. The two filer lead 204 has one conductor cable servicing the tip electrode 206 and the other conductor cable servicing the coil electrode 208. The four filer lead 202 has two conductor cables servicing the tip electrode 210 and the other two conductor cables servicing the coil electrode 212.

The leads 202 and 204 were tested under the same conditions as discussed above in connection with FIGS. 1A and 1B. The test results are shown in FIG. 2 at the various points along the leads 202, 204. The lead 202 experienced temperature increases of 24.6° C., 4.3° C., 7.2° C. and 3.1° C. at the coil proximal end, coil intermediate point, coil distal end, and tip, respectively, as noted along the lead 202. The lead 204 experienced temperature increases of 43° C., 7.6° C., 6.2° C. and 5.4° C. at the coil proximal end, coil intermediate point, coil distal end, and tip, respectively, as noted along the lead 202.

Figure 3:
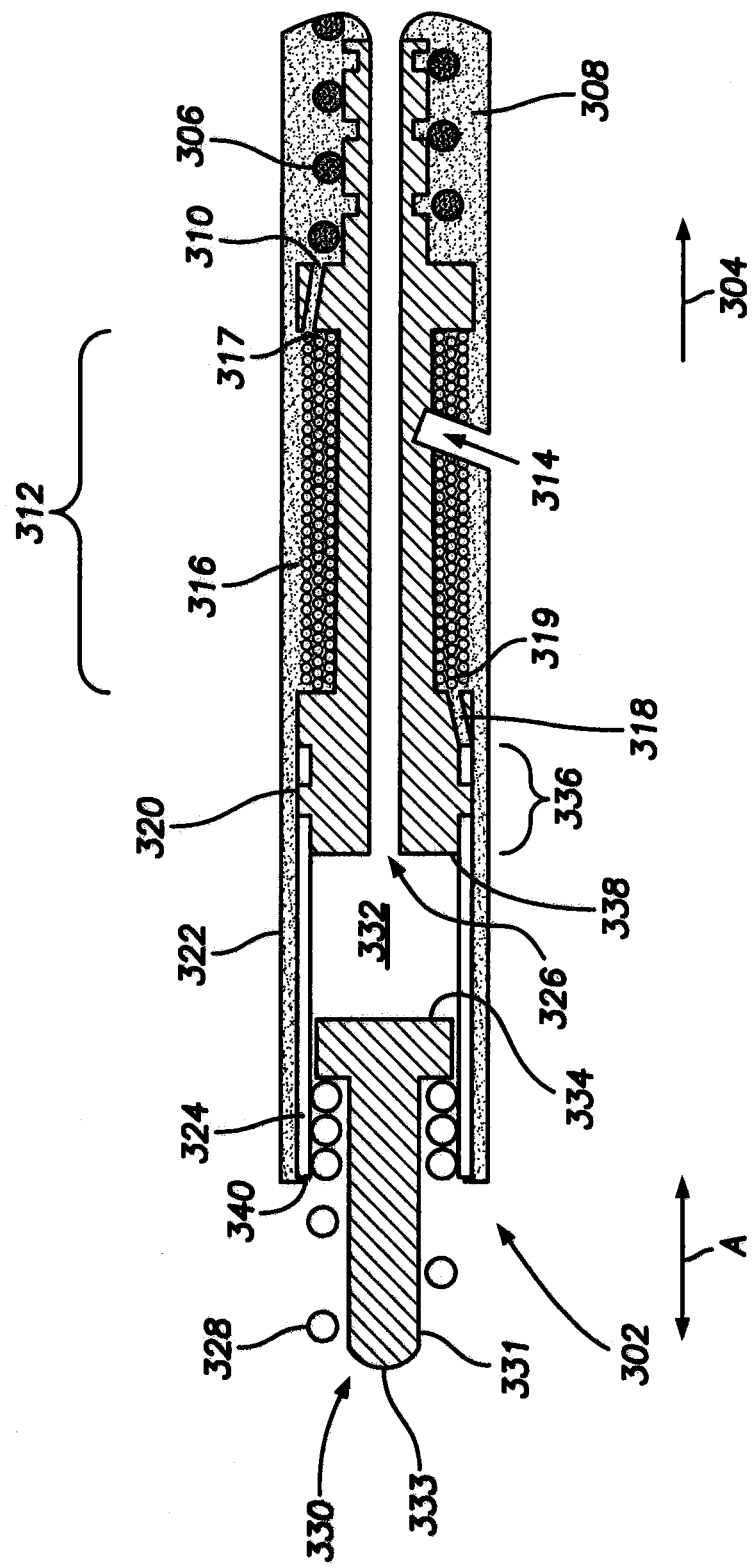
FIG. 3 illustrates a cross sectional view of a distal portion of a lead formed in accordance with an embodiment.

FIG. 3 illustrates a cross sectional view of a distal portion 300 of a lead (e.g., lead 101-104) formed in accordance with an embodiment. The distal portion 300 includes a distal end 302 with a remainder of the lead body extending in the direction of arrow 304. A helix screw 328 extends from the distal end 302 of the lead. The helix fixation screw 328 also functions as a tip electrode for sensing and delivery of therapy. The distal portion 300 includes a conductive cable 306 that extends from the proximal end of the lead where the cable 306 is joined to the IMD. A braid 308 is provided about the cable 306 and encased in insulation 322. The braid 308 affords added axial strength and torque transfer.

An inductor element 312 is provided in the distal portion 300 between an outer end of the cable 306 and the helix fixation screw 328. The inductor element 312 may be formed in various configurations and be afforded select electrical properties. The inductor element 312 electrically connects the conductor cable 306 to the fixation screw 328. Inclusion of the inductor element 312 at the distal end 302 of the lead increases the impedance, that is exhibited by the conductive path formed by the screw 328 and cable 306, at 62.5 kHz so that very little current flows from the distal end at the fixation helix screw 328.

The inductor element 312 may have the general overall structure as described in published patent application Publication No. 2011/0125240,published May 26, 2011, to Zhao et al., and titled "BIOCOMPATIBLE INDUCTOR FOR IMPLANTABLE LEAD AND METHOD OF MAKING SAME",now abandoned, the complete subject matter of which is expressly incorporated herein by reference in its entirety. The unique differences between the inductor of the '240 application and the inductor element 312, in accordance with embodiments herein, are described hereafter.

The inductor element 312 includes a bobbin 314 having a central barrel portion and flanges at opposite ends thereof. A coil 316 is wound about the barrel portion. A proximal end 317 of the coil 316 is electrically joined to the cable 306 at a crimp sleeve 310. A distal end 319 of the coil 316 is electrically joined, at a linking wire 318, to a conductive extension cylinder 324. The extension cylinder 324 is tubular in shape and has a base portion 336 that securely overlaps and engages an outer end segment 338 of the bobbin 314. The extension cylinder 324 includes an outer end 340 that electrically and physically secures to the windings of the helix fixation screw 328, thereby completing an electrical path between the cable 306 and the screw 328.

The bobbin 314 includes a central passage 326 extending entirely there through. The passage 326 aligns with a lumen that extends along the entire length of the lead such that a stylet may be inserted through the lumen in the lead, and through the passage 326 in the bobbin 314.

The extension cylinder 324 defines an interior chamber 332. An obturator 330 is provided within the screw 328 and chamber 332. For example, the obturator 330 may include a plunger base 334 that is joined in a T-shape with an obturator arm 331. The obturator 330 moves in the directions of arrow A between extended and retracted positions. As shown in FIG. 2, the obturator 330 is in the extended position with the arm 331 deployed past an outermost end of the screw 328 and the plunger base 334 slid along the chamber 332 until abutting against the base of the screw 328. The obturator 330 is advanced to, and held in, this deployed/extended position or state during implantation by a stylet that extends through the passage 326. The stylet extends through the lead from the proximal end toward the distal end in order to activate the obturator 330 (e.g., direct the obturator 330 to move to a snag prevention position).

Once the screw 328 is at a location where it is desirable to rotate the screw to engage tissue, the stylet is removed, thereby permitting the plunger base 334 to retract along the chamber 332 toward the outer end segment 338. As the plunger base 334 retracts, similarly the arm 331 and a majority of the obturator 330 to retract into the extension cylinder 324. The arm 331 includes a rounded outer end 333 that prevents tissue from snagging on the screw 328 while the obturator 330 is in the extended position.

The number of windings, coil diameter, layers of windings and the like may be varied in the inductor element 312. For example, the inductor element 312 may have an impedance of about 20 kohms at around 60 MHz. Optionally, the inductor element 312 electrical properties may be varied based on the size, type and configuration of the conductors extending along the lead, as well as based on the size, type and shape of the tip electrode.

Optionally, the fixation screw 328 may be connected to two or more cable filers. Connecting multiple cable filers to the fixation screw 328 results in less heating of the fixation screw 328 when compared to a single filer.

In accordance with embodiments herein, the lead may not include a ring electrode, hereafter referred to as a non-RV-ring configuration. Eliminating the RV ring electrode, in turn eliminates another component that will otherwise undergo RF heating during MRI imaging. Optionally, a ring electrode may be added to the lead and an inductor element added in serial conductive relation with the ring electrode and the corresponding coiled conductor cables.

Figure 4:
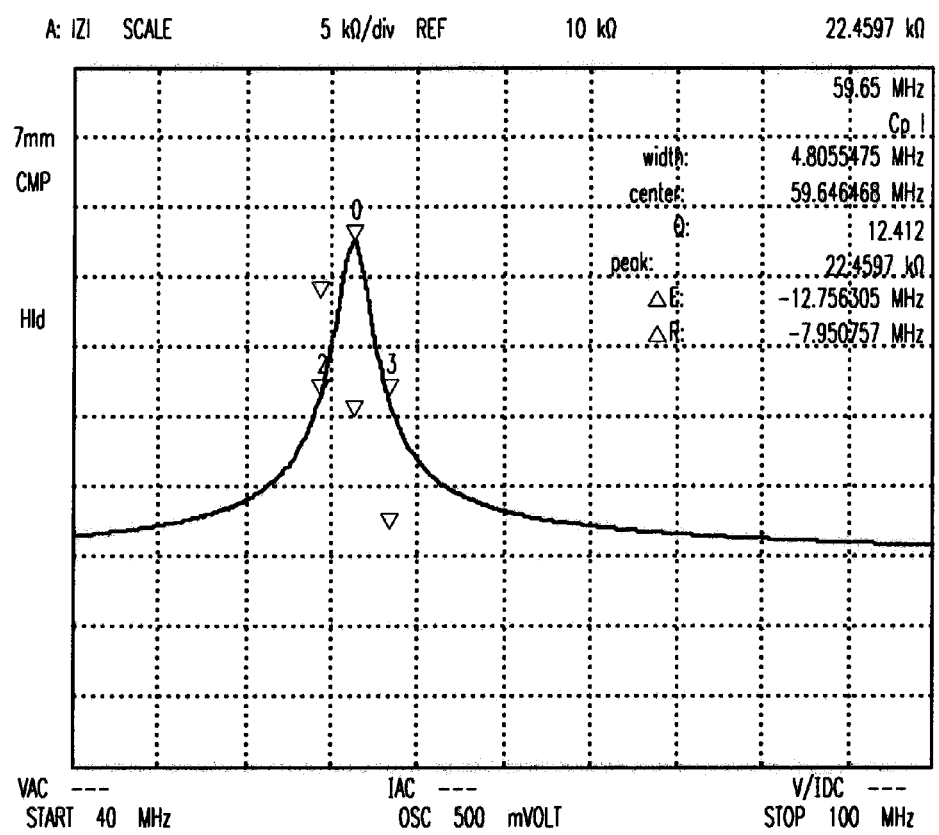
FIG. 4 illustrates a bode plot of the impedance exhibited by the inductor element in accordance with an embodiment.

FIG. 4 illustrates a Bode plot of the impedance exhibited by the inductor element 312, in accordance with an embodiment, during a frequency sweep from 40 MHz to 100 MHz. The self-resonant frequency of the inductor element 312 is around 59.6 MHz, which is relatively close to 62.5 MHz, the MRI RF frequency. The inductor element 312 in FIG. 5 has an impedance of 22.45 kohm, at 59.646 MHz, which limits heating of the distal fixation screw 328 to less than 10° C., and preferably below 5° C. and more preferably to about 2 to 3° C. when using a quad filer conductor cable.

Figure 5:
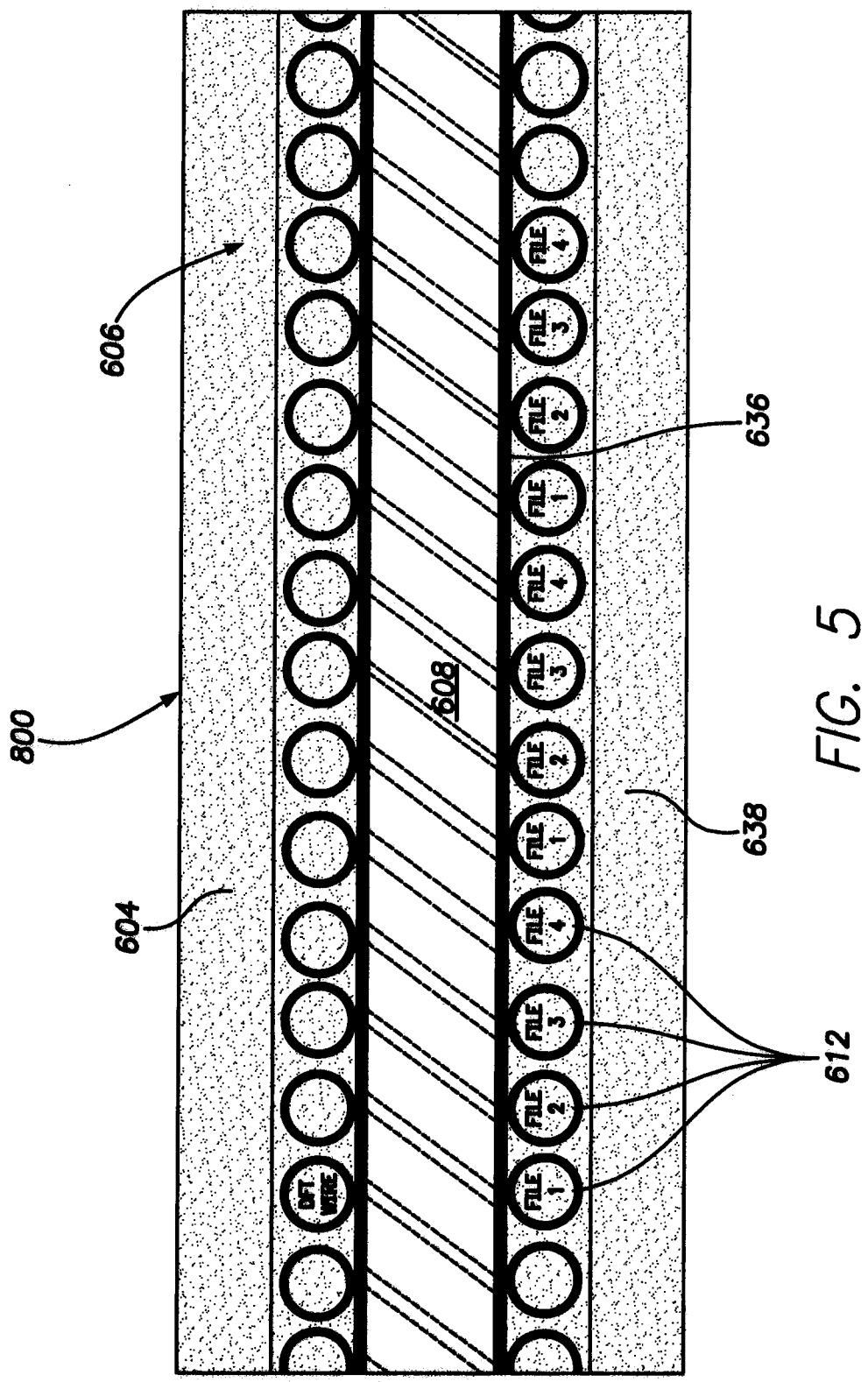
FIG. 5 illustrates a cross sectional view of a portion of a lead body in a region remote from the shocking coil electrode formed in accordance with an embodiment.
Figure 6:
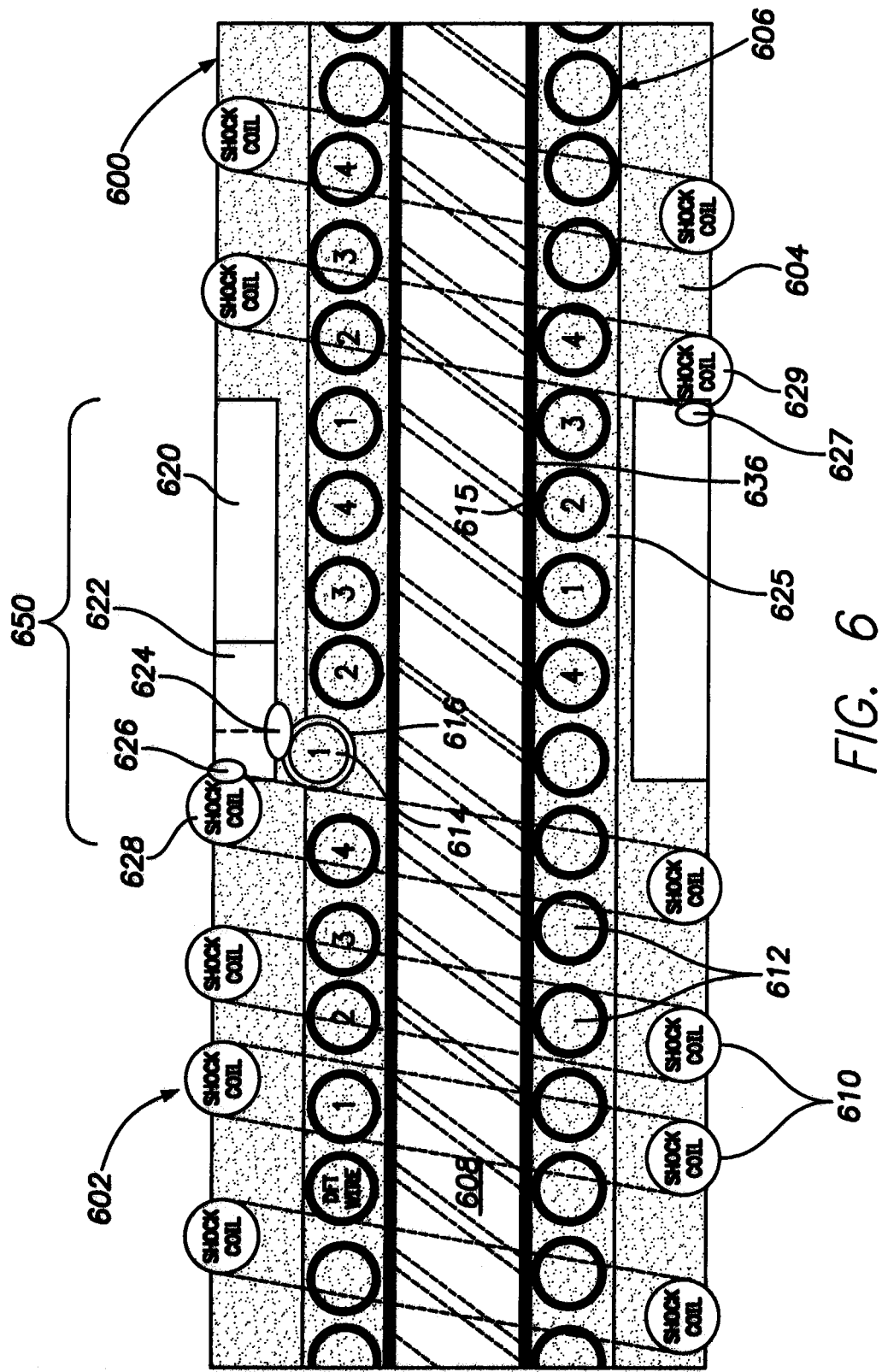
FIG. 6 illustrates a cross sectional view of a portion of a lead body in a region where a coil electrode is located.

FIG. 5 illustrates a cross sectional view of a portion of a lead body 600 in a region remote from the shocking coil electrode formed in accordance with an embodiment. The lead body 600 includes an insulation layer 604 surrounding at least one conductive cable 606 that extends along the length of the lead body 600. The cable 606 surroundings at least one central lumen 608 extending along the length of the lead body 600. The cable 606 includes windings 612 (also referred to as filers) that are arranged concentrically about the lumen 608. The layer 604 also electrically isolates the electrode turns 610 (FIG. 6) from the cable windings 612. In FIGS. 5 and 6, the cable 606 represents a "quad-filer" configuration in which four wires are coiled around a central Teflon tube 636. The four wires (or filers) are separately labeled File 1, File 2, File 3, and File 4 and are electrically separated through individual insulation. The windings 612 may be insulated from one another with the insulation layer 604.

Optionally, Teflon or FEP may be used for the liner 636 that forms the lumen 608 for the stylet. The insulated cable is coiled in a quad-filer, co-radial configuration. A woven Dacron braid 638 affords torque transfer capability for turning the lead body to screw in the fixation screw. The braid 638 also improves tensile strength. The Optim insulation 604 provides desired abrasion resistant insulation.

FIG. 6 illustrates a cross sectional view of a portion of a lead body 600 in a region where a coil electrode 602 is located. The lead body 600 includes an insulation layer 604 surrounding at least one conductive cable 606 that extends along the length of the lead body 600. The cable 606 surroundings at least one central lumen 608 extending along the length of the lead body 600. The coil electrode 602 includes turns 610 that are arranged concentrically about windings 612 of the cable 606. As noted above, the turns 610 may represent windings, a metal ribbon, a framework formed from laser cutting a tubular body and the like. The insulation layer 604 electrically isolates the electrode turns 610 from the cable windings 612 (e.g., insulated with about 0.002" thick Tefzel). In FIG. 6, the cable 606 represents a "quad-filer" configuration in which four wires are coiled around a central Teflon tube. Optionally, more or fewer filers may be used in the cable 606. The four wires may be electrically separated through individual insulation. Optionally, a Teflon tube, such as offered by Optim, may be reflowed with the aid of shrink tubing about the wires of the quad-filer. The Dacron braid 638 is shown in the lead body 600 to provide added axial strength and torque transfer capability to the body.

FIG. 6 illustrates the cable 606 in a single radial alignment. The cable 606 may include the separate filers arranged in a common spiral and with a common radius. One or more filers 614 may be fitted with a crimp tube 616 to pierce the insulation and make contact with the inner conductive wire within the filer. The crimp tube 616 affords a site at which the shocking coil 602 is electrically joined to the filer 614. A ring 620 is provided about the lead body 600. The ring 620 is located in a gap between adjacent turns 610 of the coil electrode. The ring 620 includes a hole therein that is aligned with the crimp tube 616. Laser welds 624 and 626 (or other securing means) are used to electrically and physically join the filer 614 (File #1) of the cable 606 to the winding 628 of the coil electrode 602. Laser welds 625 and 627 (or other securing means) are used to electrically and physically join the filer 615 (File #2) of the cable 606 to the winding 628 of the coil electrode 602. As explained above, in certain embodiments, more than one filer or wire may be electrically joined to the coil electrode 602 in order to further reduce heating when exposed to MR fields.

As shown in FIG. 6, the ring 620 is located at an intermediate point along the length of the coil electrode 602. It is recognized that only a portion of the coil electrode 602 is shown, with additional turns 610 extending to the left and to the right of the FIG. 6. The ring 620 defines a cable-toelectrode connection node 650 between the conductive cable 606 and the coil electrode 602 similar to the cable-to-electrode connection configurations of FIGS. 1A and 1B between the conductive cable and the coil electrodes 103A and 103A.

Optionally, a platinum shock coil electrode 602 may be wrapped on with "dummy wire" spacing of 1:1 or 2:1 and then Optim is reflowed again to provide another layer of insulation.

Figure 7:
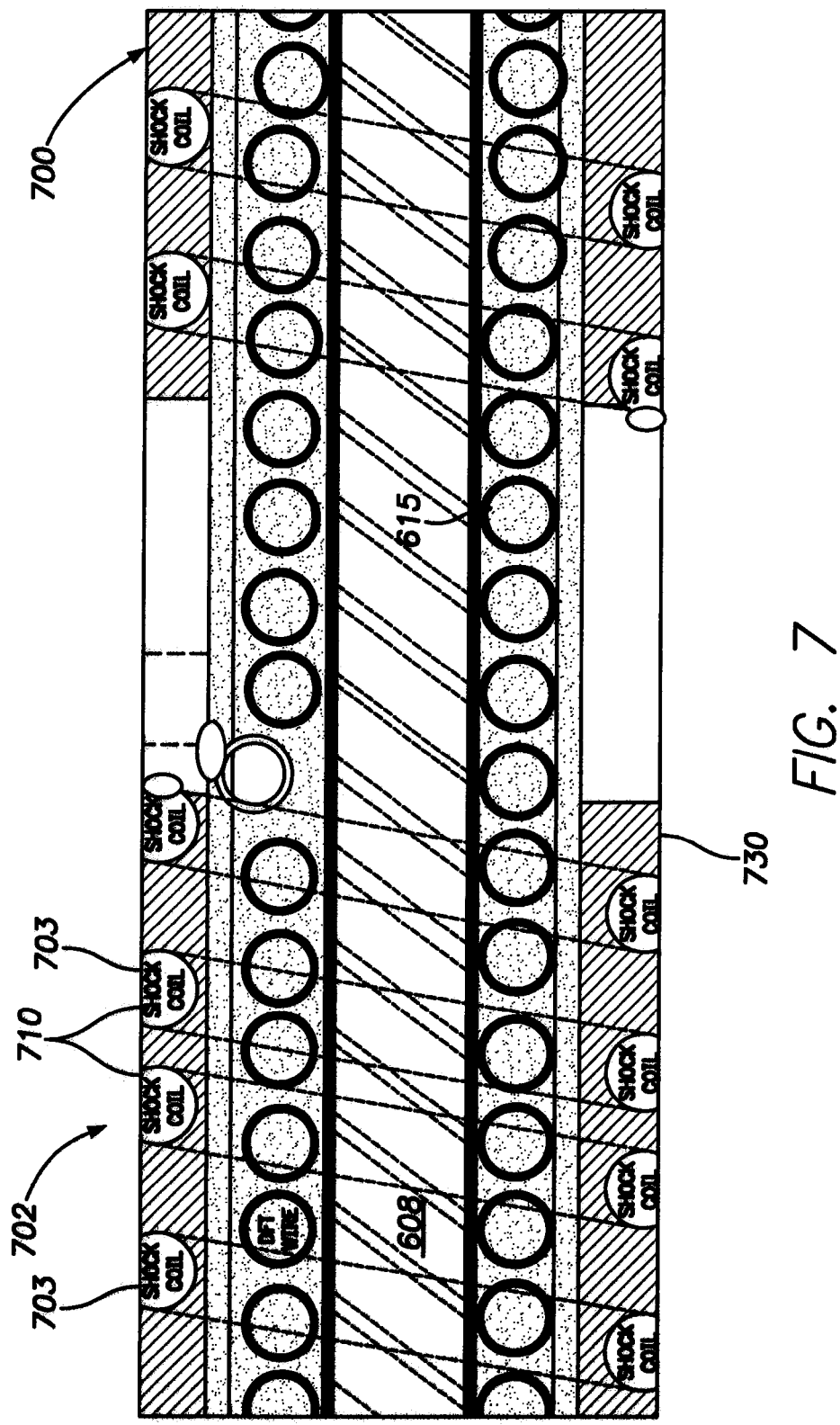
FIG. 7 illustrates a cross sectional view of an alternative embodiment for a lead body in the region under the shocking coil electrode.

FIG. 7 illustrates a cross sectional view of an alternative embodiment for a lead body 700 in the region under the shocking coil electrode 702. FIG. 7 differs from FIG. 6 in that the shocking coil 702 is "center-less ground" to afford a smooth outer surface 703 along each winding 710. Then a layer of medical adhesive silicone rubber 730 is used to fill gaps that would otherwise appear between the windings 710 of the shocking coil electrode 702. The configuration of FIG. 7 affords a softer, smoother shocking coil section. A smooth shocking coil renders the lead 700 easier to remove should a desire arise to remove the lead 700. The configuration of FIG. 7 affords a lead with reduced stiffness thereby reducing the probability that the lead 700 will damage the implant site.

Optionally, the cables within the lead may be formed various co-radial configurations such as described in Published Patent Application 2006/0229693, published Oct. 12, 2006, and titled "Medical Electrical Lead with Co-Radial Multi-Conductor Coil", the complete subject matter of which is incorporated by reference.

Figure 8:
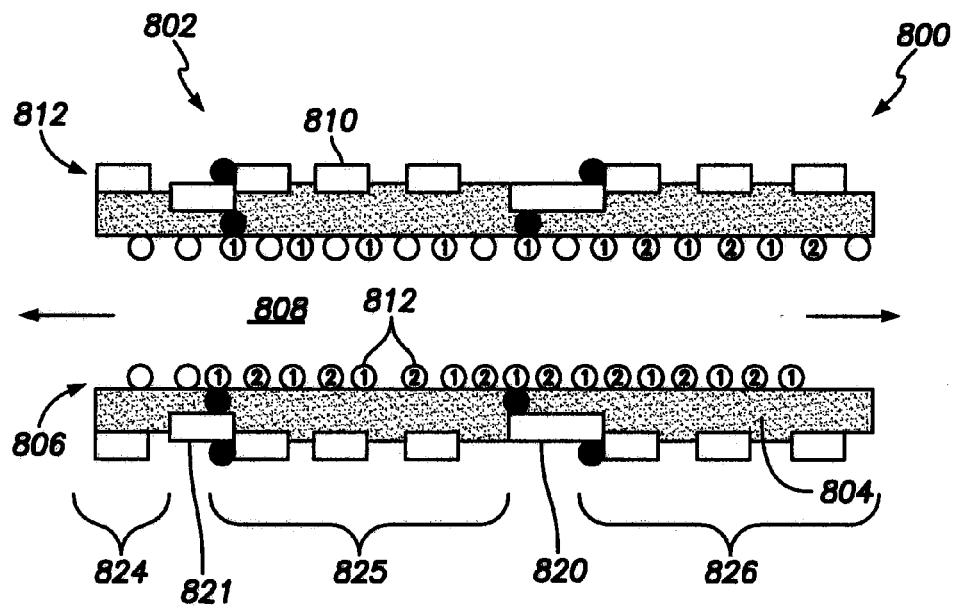
FIG. 8 illustrates a cross sectional view of a portion (the cable to electrode segment) of a lead body in a region where an electrode is located in accordance with an embodiment.

FIG. 8 illustrates a cross sectional view of a portion (the cable to electrode segment) of a lead body 800 in a region where an electrode 802 is located. The lead body 800 includes an insulation layer 804 surrounding at least one conductive cable 806 that extends along the length of the lead body 800. The cable 806 surroundings at least one central lumen 808 extending along the length of the lead body 800. The electrode 802 includes turns 810 that are arranged concentrically about turns 812 of the cable 806. The insulation layer 804 electrically isolates the electrode turns 810 from the cable windings 812.

In the example of FIG. 8, the cable 806 includes 2 filers (denoted as #1 and #2) that are interleaved or interspersed with one another. One or both filers #1 and #2 may be fitted with one or more crimp tubes at select turns of the filers #1 and/or #2. The crimp tube affords a site at which the coil 802 is electrically joined to the filer #1. Optionally, other insulation piercing, electrically conductive components may be used to pierce the insulation and form an electrical connection or coupling with the inner conductive wire within the select filer or filers.

In another embodiment, the crimp tube or other component is provided and configured to provide good electrical conduction between the filer and another structure (such as a ring), as well as provide good thermal conduction (e.g., represents a thermal conduit) between the filer and the other structure. In certain embodiments, it may be desirable to provide a thermal conduit, as well as an electrically conductive, interface between the filer and ring when it is determined that the filers are well suited to absorb heat when the lead is exposed to an MRI field.

In the example of FIG. 8, rings 820 and 821 are located at separate intermediate points along the electrode 802 such that the rings 820 and 821 thermally partition the electrode 802 into heat dissipation segments 824-826. The rings 820 and 821 may be located in gaps between adjacent turns 810 of the electrode 802. Alternatively, the rings 820 and 821 may be located radially inward and concentric with the turns 810 of the electrode 802. In the example of FIG. 8, the first filer #1 is electrically (and thermally) joined to both of the rings 820 and 821.

Optionally, two or more filers #1 and #2 may be electrically (and thermally) joined to both of the rings 820 and 821. Optionally, one filer #1 (or a subset of filers) may be electrically and thermally joined to ring 820 and another filer #2 (or another subset of filers) may be electrically and thermally joined to the ring 821. Optionally, when multiple filers are provided in the cable, a first subset of filers may be connected to one ring (or a first group of rings) and second separate and different subset of filers may be connected to another ring (or a second group of rings).

Figure 9:
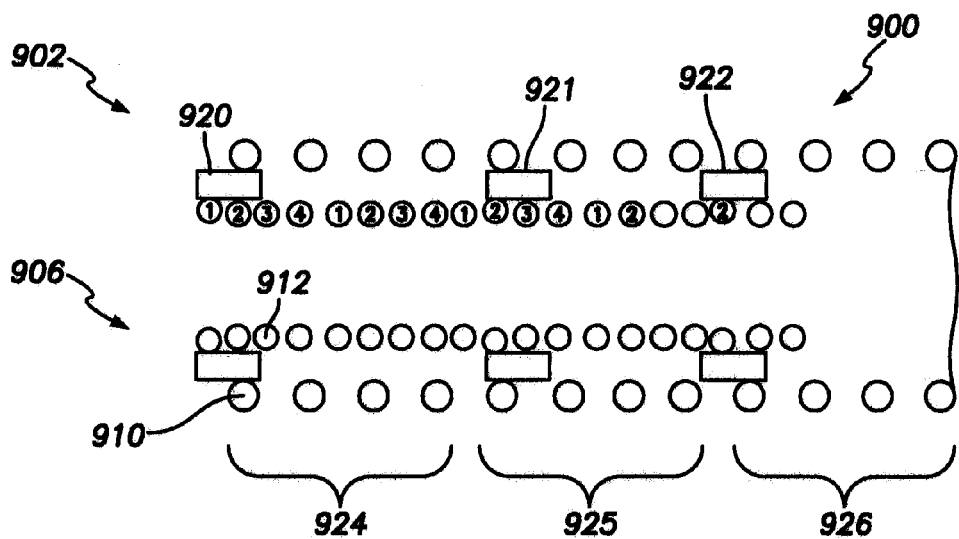
FIG. 9 illustrates a cross sectional view of a portion (the cable to electrode segment) of a lead body in a region where a coil electrode is located in accordance with an embodiment.

FIG. 9 illustrates a cross sectional view of a portion (the cable to electrode segment) of a lead body 900 in a region where a coil electrode 902 is located. The lead body 900 includes at least one conductive cable 906 that extends along the length of the lead body 900. The electrode 902 includes turns 910 that are arranged concentrically about windings 912 of the cable 906. The insulation layer (not shown) electrically isolates the electrode turns 910 from the cable windings 912. In the example of FIG. 9, the cable 906 includes 4 filers (as denoted #1-#4) that are interwoven with one another. One, multiple or all of the filers #1-#4 may be directly, or indirectly (through a crimp tube or other component) electrically (and optionally thermal) coupled to the turns 910 of the electrode 902. Rings 920-922 are located at separate intermediate points along the electrode 902 to partition the electrode 902 into heat dissipation segments 924-926.

In at least one embodiment, the crimp tube or other component is provided and configured to provide good electrical conduction between the filer and another structure (such as a ring).

The filers #1-#4, rings 920-922, and segments 924-926 may be coupled in a series or "daisy chain" manner. For example, a first filer (e.g., #1) may be connected to a first ring 920 which is connected to a proximal end of the first segment 924. The distal end of the first segment 924 is connected to a second ring 921 that is connected to a second filer #2. The second filer #2 is connected to a third ring 922 that is connected to a proximal end of a third segment 926. Optionally, the filers #1-#4, rings 920-922, and segments 924-926 may be connected in different combinations in electrical and thermal series.

Figure 10:
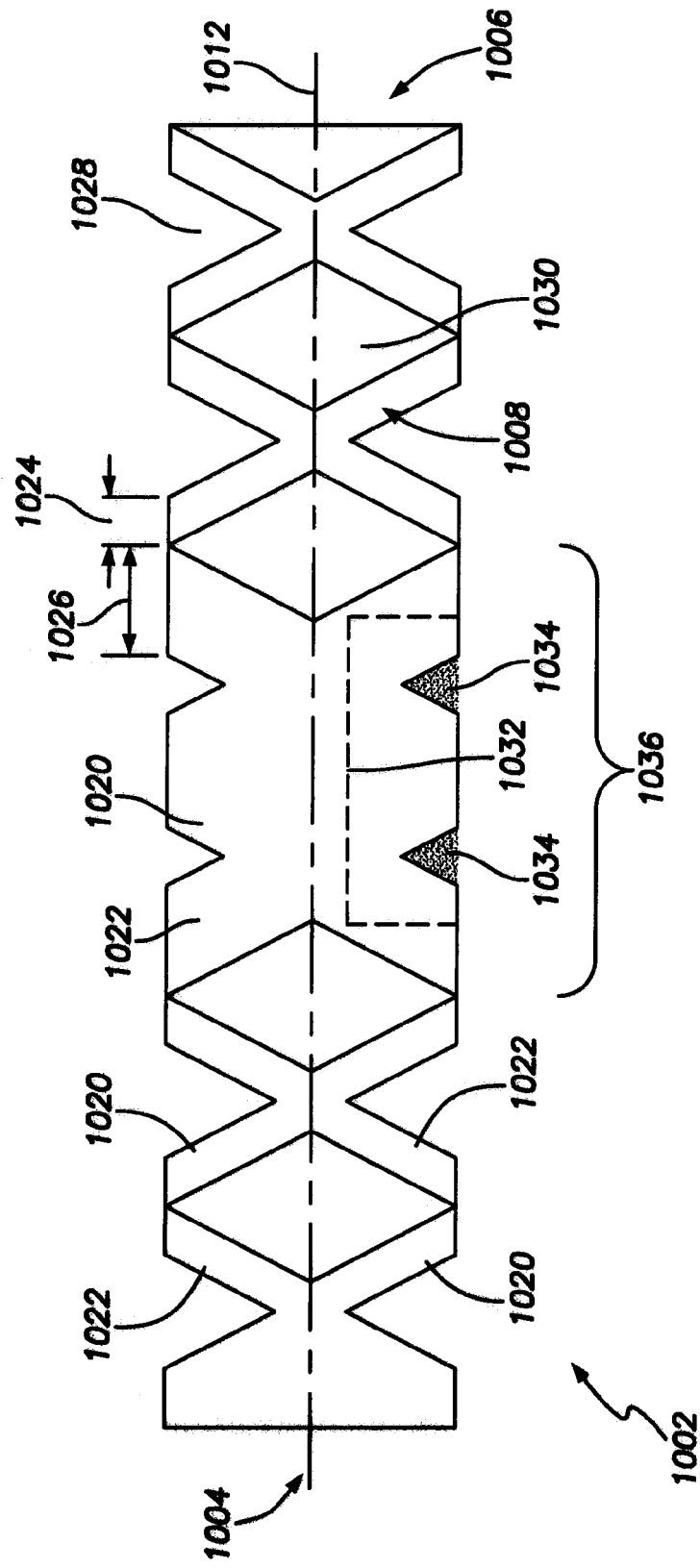
FIG. 10 illustrates a side view of an electrode formed in accordance with an alternative embodiment.

FIG. 10 illustrates a perspective view of an electrode 1002 formed in accordance with an alternative embodiment. The electrode 1002 may be wound, stamped and formed, laser cut from a tubular conductive stock material, or otherwise manufactured to arrive at a desired framework. The electrode 1002 includes proximal and distal ends 1004 and 1006 with a lattice framework 1008 extending there between. The lattice framework is defined by a collection of turns 1020 and 1022 that extend about a longitudinal axis 1012. The turns 1020 and 1022 fold about the longitudinal axis and are distributed such that a first portion of the turns 1020 are oriented to extend at an acute angle toward the proximal end 1004, while a second portion of the turns 1022 are oriented to extend at an acute angle toward the distal end 1006. The turns 1020 and 1022 intersect to form generally "X shaped" intersections. The turns 1020 and 1022 are separated by notched openings 1028 and 1030 that are stamped or cut to form the turns 1020 and 1022. A ring 1032 is provided below the electrode 1002 and aligned with the segment 1036 of the electrode 1002. The ring 1032 is electrically coupled to the turns 1020 and 1022 in the segment 1036.

In the example of FIG. 10, the turns 1020 and 1022 have been made with various thicknesses 1024 and 1026. The thickness of the turns 1020 and 1022 (as well as the thickness of the turns for any electrode described herein) may differ in separate segments of the electrode 1002. For example, the turns 1020 and 1022 in the segment 1036 may be formed thicker than the turns 1020 and 1022 along either side of the segment 1036. Varying the thickness 1026 and 1024 of the turns 1020 and 1022 in different regions of the electrode may facilitate energy transfer in the regions where the turns 1020 and 1022 are thicker. For example, in the region where the turns 1020 and 1022 are joined to the ring 1032, increasing the thickness may increase energy transfer from the ring 1032 into the electrode 1002.

Figure 11:
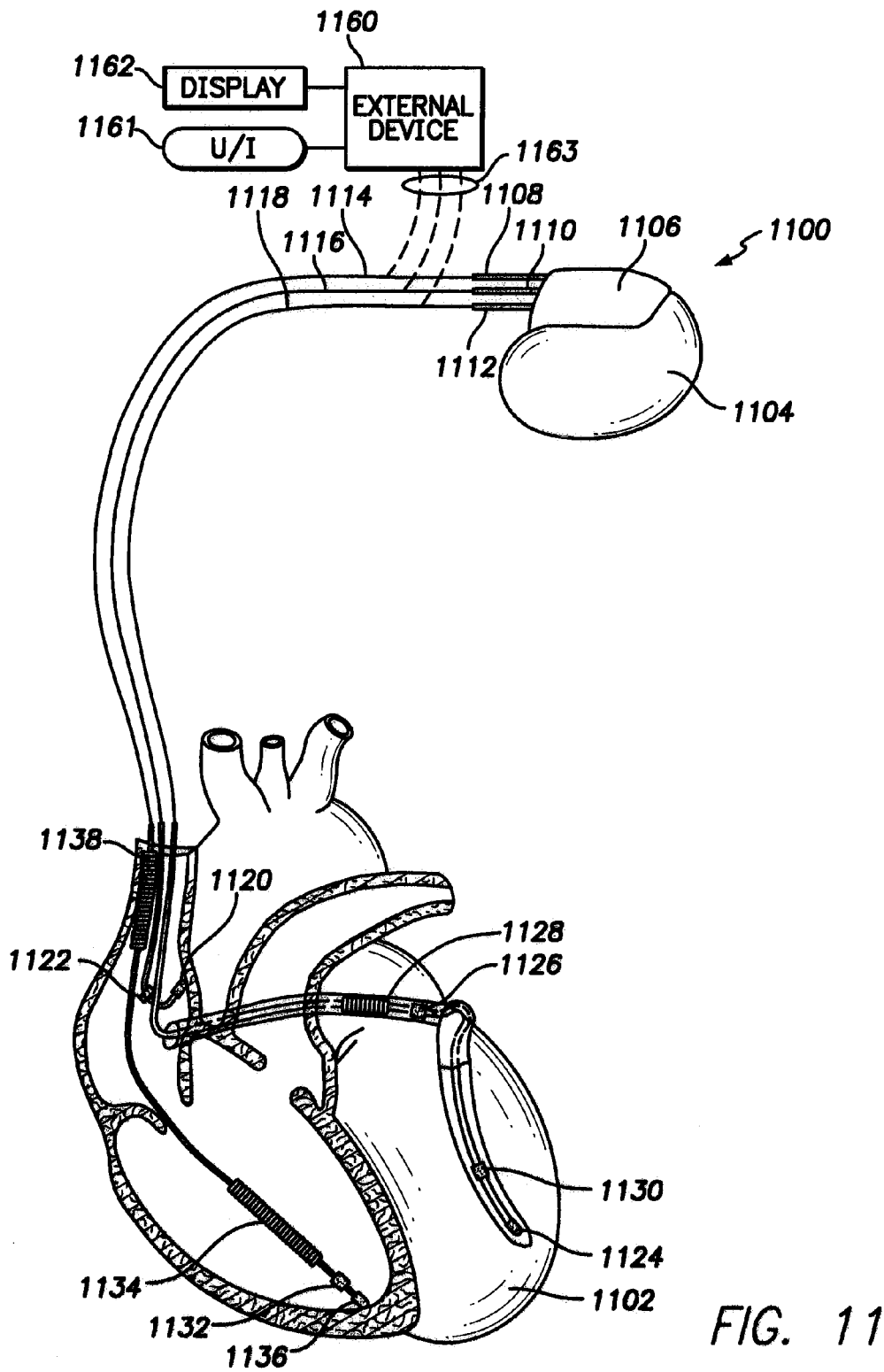
FIG. 11 illustrates an implantable medical device (IMD) and external device coupled to a lead implemented in accordance with one embodiment.

It is understood that the thickness of the turns of the electrodes described in connection with each embodiment herein may be varied such that turns in at least a first select segment (or segments) of the electrode have a first thickness while turns in at least a second segment (or segments) have a second greater thickness (radially toward the center of the electrode and/or longitudinally along the length of the electrode). In the example of FIG. 10, the turns 1020, 1022 in the segment 1036 coupled or proximate to the ring(s) 1032 were formed to be thicker than turns 1020, 1022 in segments near the proximal and distal ends 1004 and 1006 and remote from the rings 1032. Alternatively, the turns 1020, 1022 in the segments near one or both of the proximal and distal ends 1004 and 1006 may be formed to be thicker than the turns 1020, 1022 in the segment(s) 1036 near the ring(s) 1032. FIG. 11 illustrates an IMD 1100 and external device 1160 coupled to a heart 1102 in a patient and implemented in accordance with one embodiment. The external device 1160 may be a programmer, an external defibrillator, a workstation, a portable computer, a personal digital assistant, a cell phone and the like. The IMD 1100 may be a cardiac pacemaker, an ICD, a defibrillator, an ICD coupled with a pacemaker, and the like, implemented in accordance with one embodiment. The IMD 1100 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 1100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like.

The IMD 1100 includes a housing 1104 that is joined to a header assembly 1106 that holds receptacle connectors 1108, 1110, 1112 connected to a right ventricular lead 1114, a right atrial lead 1116, and a coronary sinus lead 1118, respectively. The leads 1114, 1116, and 1118 measure cardiac signals of the heart 1102. The right atrial lead 1116 includes an atrial tip electrode 1120 and an atrial ring electrode 1122. The coronary sinus lead 1118 includes a left ventricular tip electrode 1124, a left atrial ring electrode 1126, and a left atrial coil electrode 1128. The coronary sinus lead 1118 also is connected with an LV ring electrode 1130 disposed between the LV tip electrode 1124 and the left atrial ring electrode 1126. The right ventricular lead 1114 has an RV tip electrode 1136, an RV ring electrode 1132, an RV coil electrode 1134, and an SVC coil electrode 1138. The leads 1114, 1116, and 1118 detect IEGM signals that form an electrical activity indicator of myocardial function over multiple cardiac cycles.

During implantation, the external device 1160 is connected to one or more of the leads 1114, 1116, 1118 through temporary inputs 1163. The inputs 1163 of the external device 1160 receive IEGM signals from the leads 1114, 1116, 1118 during implantation and displays the IEGM signals to the physician on display 1162. Optionally, the external device 1160 may not be directly connected to the leads 1114, 1116 and 1118. Instead, the IEGM cardiac signals sensed by the leads 1114, 1116 and 1118 may be collected by the IMD 1100 and then transmitted wirelessly to the external device 1160. Hence, the external device 1160 receives the IEGM cardiac signals through telemetry circuit inputs. The physician or another user controls operation of the external device 1160 through a user interface 1161 and display 1162.

It is to be understood that the invention is not limited in its application to the details of construction and the arrangement of components set forth in the description herein or illustrated in the drawings hereof. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The terms "couple" and "connect" as used throughout to describe attachment between the cables, rings and electrodes, refer to direct abutting engagement as well as proximate indirect engagement between the cable and the rings, and rings and turns. For example, a connection may be made by providing a solder or weld bead or other affixation medium between a ring and cable filer, or ring and electrode turn. The cable filers, rings and electrode turns are considered coupled or connected within the context of the present specification so long as electrical and thermal energy transfer therebetween in a manner sufficient to distribute MRI field induced energy and heat along segments of the electrode as described herein.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Also, it is to be understood that phraseology and terminology used herein with reference to device or element orientation (such as, for example, terms like "central," "upper," "lower," "front," "rear," "distal," "proximal," and the like) are only used to simplify description of the present invention, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

The invention claimed is:

1. An implantable lead, comprising:
   a lead body configured to be implanted in a patient, the lead body having a distal end and a proximal end, and a lumen extending between the distal and proximal ends;
   a connector assembly provided at the proximal end of the lead body, the connector assembly configured to connect to an implantable medical device;
   an electrode comprising a shocking coil provided along the lead body at a position intermediate between the distal end and the proximal end of the lead body, the electrode having a length extending between a proximal end and a distal end of the electrode;
   a conductor cable located within the lead body and extending at least partially along a length of the lead body; and
   an connection node electrically connecting the cable to the electrode within an intermediate segment along the length of the electrode, the connection node disposed at a position intermediate between the proximal and distal ends of the electrode.

2. The lead of claim 1, wherein the cable includes a distal end that is joined at the connection node to the intermediate point along the electrode.

3. The lead of claim 1, wherein the shocking coil includes turns that extend in about the lead body, the connection node electrically coupled to an intermediate turn within the electrode.

4. The lead of claim 1, wherein the electrode includes turns that extend about the lead body, the cable being electrically connected at first and second connection nodes to first and second intermediate turns spaced apart from one another and apart from the distal and proximal ends of the electrode.

5. The lead of claim 1, wherein the electrode includes turns and the connection node includes a conductive ring provided about the lead body, the connection node being positioned between adjacent intermediate turns of the electrode, the ring being electrically connected to the cable and electrically connected to at least one turn of the electrode.

6. The lead of claim 1, wherein the cable includes at least first and second filers, the first and second filers including distal ends connected at the connection node to the electrode.

7. The lead of claim 1, wherein the cable includes at least first and second filers, the first and second filers including distal ends connected at first and second separate connection nodes to the electrode, respectively.

8. The lead of claim 1, wherein the lead included a connector at proximal end, the connector configured to be connected to at least one of an implantable or external medical device, the lead representing at least one of a catheter, an ICD lead, a neurostimulation lead, a pacemaker lead and a defibrillator lead, the electrode representing a high energy shocking coil.

* * * * *